US006822093B2

(12) United States Patent
Song et al.

(10) Patent No.: US 6,822,093 B2
(45) Date of Patent: Nov. 23, 2004

(54) SYNTHESIS OF HETEROARYLAMINE INTERMEDIATE COMPOUNDS

(75) Inventors: Jinhua J. Song, Brewster, NY (US); Nathan K. Yee, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 173 days.

(21) Appl. No.: 10/313,666

(22) Filed: Dec. 6, 2002

(65) Prior Publication Data

US 2003/0135046 A1 Jul. 17, 2003

Related U.S. Application Data

(63) Continuation-in-part of application No. 09/735,160, filed on Dec. 12, 2000, now Pat. No. 6,635,767.
(60) Provisional application No. 60/206,327, filed on May 23, 2000.

(51) Int. Cl.$^7$ .............................................. C07D 413/06
(52) U.S. Cl. ........................ 544/122; 544/60; 544/124; 544/242; 544/333; 546/143; 546/159; 546/193; 546/194; 546/268.4; 546/273.4; 546/277.4; 546/281.1; 546/282.7
(58) Field of Search ........................ 544/60, 122, 124, 544/242, 333; 546/143, 159, 193, 194, 268.4, 273.4, 277.4, 281.1, 282.7

(56) References Cited

FOREIGN PATENT DOCUMENTS

| WO | WO 98/52558 | 11/1998 |
|----|-------------|---------|
| WO | WO 00/55139 | 9/2000  |

OTHER PUBLICATIONS

William E. Parham, et al; Selective Halogen–Lithium Exchange in 2,5–Dibromobezenes and 2,5–Dibromopyridine, J. Org. Chem., vol. 42, No. 2 1977, pp. 257–260.
Francois Tracourt, et al; Pyridylmagnesium Chlorides from Bromo and Dibromopyridines by Bromine Magnesium Exchange: A convenient Access to Functionalized Pyridines, Tetrahedron Letters 40, pp 4330–4342, Feb. 18, 1999.
Robert C. Corcoran et al; Iodopyridines from Bromo and Chloropyridines, Tetrahedron Letters vol. 31, No. 47, pp. 6757–6758, 1990.
Uwe Lehmann, et al; 5,5"Disubstituted 2,2';6',2"–Terpyridines through and for Metal Mediated Cross–Coupling Chemistry, Chem. Eur. J. 1999, 5, No. 3, pp 854–859.
Francis H.Case: The Synthesis of Certain Substituted 2,2' Blpyridyls, Chemistry Department of Temple University, vol. 68, pp 2574–2577.
Wilson Baker, et al: Condensation Products of Phenois and Ketones. Part VII. Molecular Complexes fomed by 2' Hydroxy–2:4:4:7:4'–pentamethylflavan, pp 83–87.
Harry Heaney et al; The Generation of Iminium Ions Using Chlorosilanes and their Reactions with Electron Rich Aromatic Heterocycles, Tetrahedron, vol. 53, No. 8, pp 2941–2958, 1997.
Henri Sliwa and Dominique Blondeau, Synthesis and NMR Study of Mannich Bases of 8–Acetoxy–Indolizines, Heterocycles, vol. 16, No. 12, pp 2159–2167, 1981.
John L. Roberts, et al; Addition of Grigard and Lithium Reagents to Eschenmoser's Salt, A Convenient Synthesis of Terminal Olefins, Tetrahedron Letters No. 15, pp 1299–1302, 1977.
Martin et al; NMR Study of heterocyclic organomagnesium in the furan, thiophene, selenophene, and pyridine series, J. Organometallic Chemistry, 67(3), pp. 327–339, 1974.
Y. Yang, et al; Synthesis of 5–Arylated Indoles via Palladium–Catalyzed Cross–Coupling Reaction of 5–IndolyBoronic Acid with Aryl and Heteroaryl Halides, Heterocyucles; vol. 34, No. 7, 1992–XP002036319.
D. Cal, et al; A Study of the Lithlation of 2,6 Dibromopyridine with Butyllithium and its Application to Synthesis of L–739–010, Tetrahedron Letters vol. 37, No. 15, pp 2537–2540, 1996.
S. Hargreaves, et al; the Synthesis of Substituted Pyridylpyrimidine Fungicides Using Palladium–Catalysed Cross--Coupling Reactions, Tetrahedron Letters 41 (2000) 1653–1656.

*Primary Examiner*—Deepak Rao
(74) *Attorney, Agent, or Firm*—Robert P. Raymond; Anthony P. Bottino; Timothy X. Witkowski

(57) ABSTRACT

Disclosed are novel 2-(5-halopyridyl) and 2-(5-halopyrimidinyl) magnesium halides, processes of making and their use in the efficient synthesis in their respective 5-halo-2-substituted pyridines and pyrimidines.

8 Claims, No Drawings

SYNTHESIS OF HETEROARYLAMINE INTERMEDIATE COMPOUNDS

APPLICATION DATA

This application is a continuation in-part of U.S. application Ser. No. 09/735,160 filed Dec. 12, 2000 now U.S. Pat. No. 6,635,767.

FIELD OF INVENTION

The present invention relates to synthesis of heteroarylamine intermediate compounds.

BACKGROUND OF THE INVENTION

Aryl- and heteroaryl-substituted ureas have been described as inhibitors of cytokine production. These inhibitors are described as effective therapeutics in cytokine-mediated diseases, including inflammatory and autoimmune diseases. Examples of such compounds are reported in WO 99/23091 and in WO 98/52558.

A key step in the synthesis of these compounds is the formation of the urea bond. Various methods have been reported to accomplish this. For example, as reported in the above references, an aromatic or heteroaromatic amine, II, may be reacted with an aromatic or heteroaromatic isocyanate III to generate the urea IV (Scheme I)

Scheme I

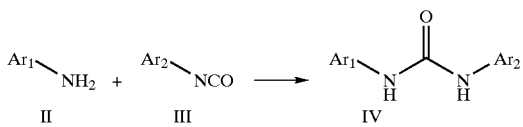

If not commercially available, one may prepare the isocyanate III by reaction of an aryl or heteroaryl amine Ar$_2$NH$_2$ with phosgene or a phosgene equivalent, such as bis(trichloromethyl) carbonate (triphosgene) (P. Majer and R. S. Randad, J. Org. Chem. 1994, 59, 1937) or trichloromethyl chloroformate (diphosgene) (K. Kurita, T. Matsumura and Y. Iwakura, J. Org. Chem. 1976, 41, 2070) to form the isocyanate III, followed by reaction with Ar$_1$NH$_2$ to provide the urea. Other approaches to forming the urea reported in the chemical literature include reaction of a carbamate with an aryl or heteroaryl amine, (see for example B. Thavonekham, Synthesis, 1997, 1189 and T. Patonay et al., Synthetic Communications, 1996, 26, 4253) as shown in Scheme II below for a phenyl carbamate. U.S. patent application Ser. No. 09/611,109 also discloses a process of making heteroaryl ureas by reacting particular carbamate intermediates with the desired arylamine.

Scheme II

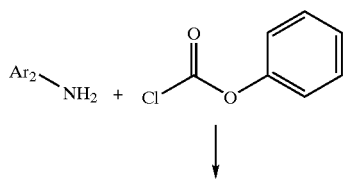

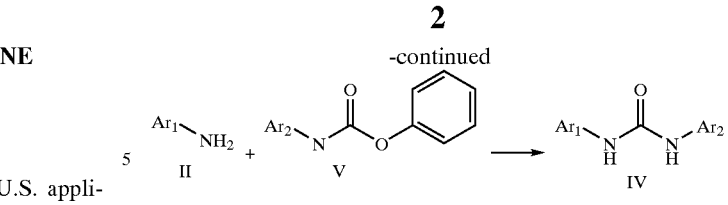

U.S. application Ser. No. 09/505,582 and PCT/US00/03865 describe cytokine inhibiting ureas of formula (I).

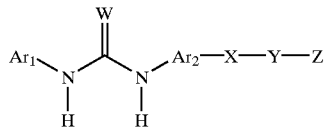

An Ar$_2$NH$_2$ required to prepare preferred compounds described therein is illustrated as formula (A).

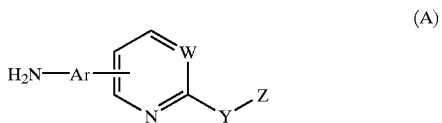

(A)

wherein W, Y, and Z are described below.

The synthesis of II, a preferred formula (A) intermediate was described in U.S. application Ser. No. 09/505,582 and PCT/US00/03865 and is illustrated in Scheme III.

Scheme III

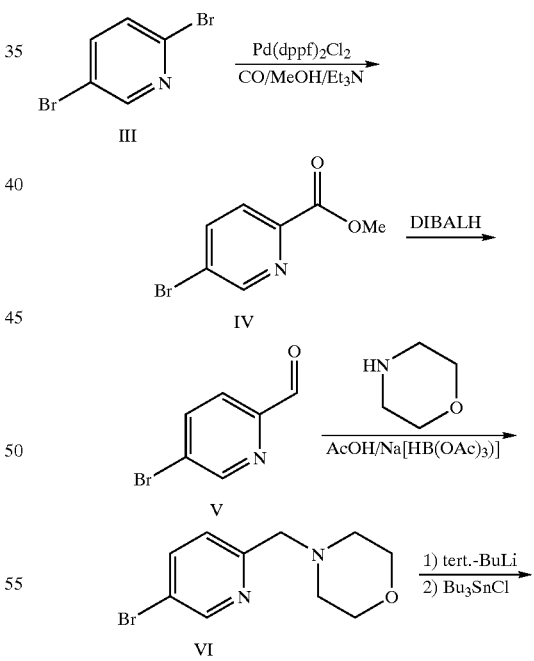

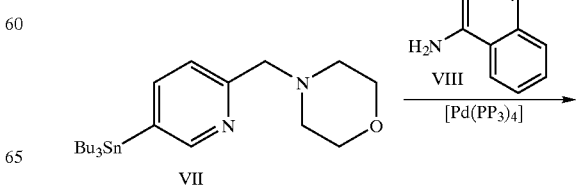

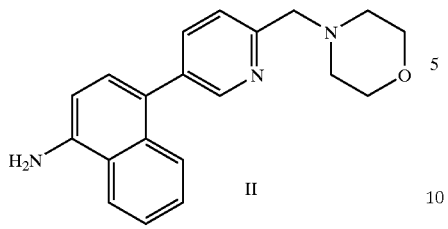

II

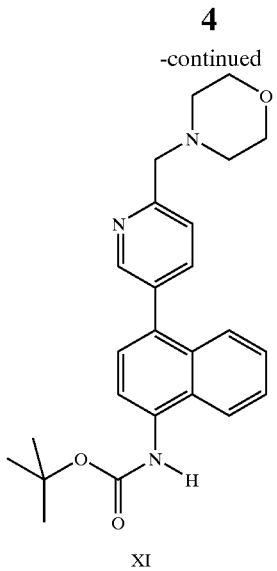

XI

HCl, dioxane
―――――――→
NaOH

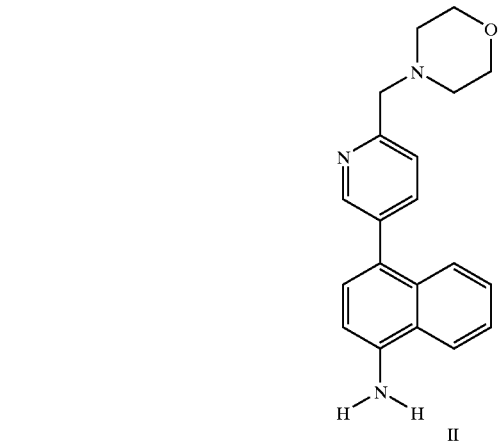

II

The synthesis begins with a palladium catalyzed carbonylation of 2,5-dibromopyridine (III) to provide ester IV in 55% yield. The reaction is run under pressure (80 psi CO) and must be monitored to minimize formation of the diester, an unwanted by-product. Reduction of IV with diisobutylaluminum hydride at −78° C. provides aldehyde V. This is followed by reductive amination to give VI.

Intermediate VI is then converted to II by reaction with t-BuLi at −78° C. followed by tributyltin chloride to give tributylstannane VII, followed by palladium catalyzed Stille coupling with intermediate VIII to give II. Conversion of VI and analogous intermediates to other intermediates of formula II via Suzuki coupling is also described in U.S. application Ser. No. 09/505,582 and PCT/US00/03865 (Scheme IV). According to this method, intermediate IX is treated with n-BuLi followed by trimethylborate to give arylboronic acid X. Palladium catalyzed Suzuki coupling with VI provides XI, which is deprotected by treatment with acid to give II.

Scheme IV

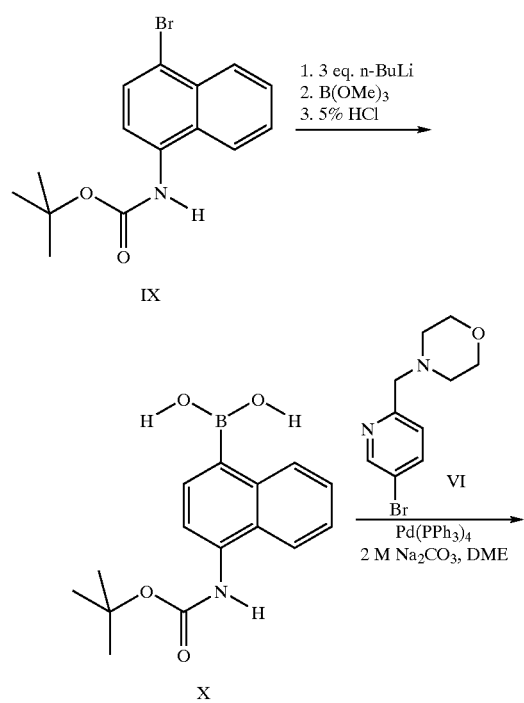

This process is not well-suited for large-scale and commercial use for several reasons. One reaction (Scheme III) is run under high pressure (80 psi) and another at extreme temperature (−78° C.). The yield of IV is only moderate and by-product formation requires a purification step. These factors, plus the cost of starting materials and reagents make this process too costly for commercial scale.

The preparation of 2-bromo-5-lithiopyridine via reaction of 2,5-dibromopyridine with n-BuLi at −100° C. has been described (W. E. Parham and R. M. Piccirilli, *J. Org. Chem.*, 1977, 42, 257). The selective formation of 2-bromo-5-pyridinemagnesium chloride via reaction with 2,5-dibromopyridine with i-PrMgCl at 0° C.—rt has also been reported (F. Trecourt et al., *Tetrahedron Lett.*, 1999, 40, 4339). In these cases, the metal-halogen exchange occurred exclusively at the 5 position of the pyridine ring. However, the syntheses of 5-bromo-2-pyridinemagnesium chloride and 5-chloro-2-pyridinemagnesium chloride have not been reported previously.

The preparation of a lithium intermediate 5-chloro-2-lithiopyridine from 2-bromo-5-chloropyridine, has been reported (U. Lehmann et al., *Chem., Euro. J.*, 1999, 5, 854). However, this synthesis requires reaction with n-BuLi at −78° C. The preparation of the 5-bromo-2-lithiopyridine from 2,5-dibromopyridine was reported by X. Wang et al. (*Tetrahedron Letters*, 2000, 4335). However, the method requires cryogenic and high dilution conditions. The selectivity was also dependent on reaction time. It is not suitable for large scale synthesis.

The synthesis of the intermediate 5-bromo-2-iodopyridine by refluxing 2,5-dibromopyridine in HI has been reported (U. Lehmann, ibid). A process using milder conditions for preparing 2-iodopyridine from 2-chloro or 2-bromopyridine has been described (R. C. Corcoran and S. H. Bang, *Tetrahedon Lett.*, 1990, 31, 6757).

SUMMARY OF THE INVENTION

It is an object of the invention to provide novel 2-(5-halopyridyl) and 2-(5-halopyrimidinyl) magnesium halides, novel methods of producing them, and to provide a novel method of using said halides in the efficient synthesis of their respective 5-halo-2-substituted pyridines and pyrimidines.

It also an object of the invention to provide a novel method of producing heteroaryl amines of the formula(A)

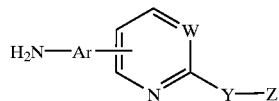

(A)

wherein Ar, W, Y and Z are described below, the heteroaryl amines are useful in the production of heteroaryl ureas as mentioned above.

DETAILED DESCRIPTION OF THE PREFERRED EMBODIMENTS

This invention relates to a novel strategy for the synthesis of heteroarylamine compounds of the formula (A) which constitute the key component of pharmaceutically active compounds possessing a heteroaryl urea group.

The invention therefore provides for processes of making a compound of the formula(A)

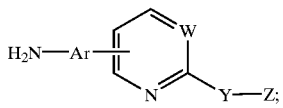

(A)

wherein:

W is $CR_3$ or N, wherein $R_3$ is chosen from hydrogen, $C_{1-5}$alkyl, $C_{1-5}$alkoxy, aryl$C_{0-5}$alkyl and —$COR_4$ wherein $R_4$ is chosen from $C_{1-5}$alkyl, $C_{1-5}$alkoxy, aryl$C_{0-5}$alkyl and amino which is optionally independently di-substituted by $C_{1-5}$alkyl, and aryl$C_{0-5}$alkyl; W is preferably CH or N, Ar is chosen from phenyl, naphthyl, quinolinyl, isoquinolinyl, tetrahydronaphthyl, tetrahydroquinolinyl, tetrahydroisoquinolinyl, benzimidazolyl, benzofuranyl, dihydrobenzofuranyl, indolinyl, benzothienyl, dihydrobenzothienyl, indanyl, indenyl and indolyl each being optionally substituted by one or more $R_1$ or $R_2$;

Y is chosen from a bond and a $C_{1-4}$ saturated or unsaturated branched or unbranched carbon chain optionally partially or fully halogenated, wherein one or more methylene groups are optionally replaced by O, N, or $S(O)_m$ and wherein Y is optionally independently substituted with one to two oxo groups, phenyl or one or more $C_{1-4}$ alkyl optionally substituted by one or more halogen atoms;

wherein when Y is the carbon chain, the left side terminal atom of Y is a carbon (the atom which is covalently attached to the heterocycle possessing W):

Z is chosen from:

aryl, heteroaryl chosen from pyridinyl, piperazinyl, pyrimidinyl, pyridazinyl, pyrazinyl, imidazolyl, pyrazolyl, triazolyl, furanyl, thienyl and pyranyl and heterocycle chosen from tetrahydropyrimidonyl, cyclohexanonyl, cyclohexanolyl, 2-oxo- or 2-thio-5-aza-bicyclo[2.2.1 ]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholinyl, thiomorpholinyl, thiomorpholinyl sulfoxidyl, thiomorpholinyl sulfonyl, piperidinyl, piperidinonyl, pyrrolidinyl and dioxolanyl, each of the aforementioned Z are optionally substituted with one to three halogen, $C_{1-6}$ alkyl, $C_{1-6}$ alkoxy, $C_{1-3}$ alkoxy-$C_{1-3}$ alkyl, $C_{1-6}$ alkoxycarbonyl, aroyl, $C_{1-3}$acyl, oxo, pyridinyl-$C_{1-3}$ alkyl, imidazolyl-$C_{1-3}$ alkyl, tetrahydrofuranyl-$C_{1-3}$ alkyl, nitrile-$C_{1-3}$ alkyl, nitrile, phenyl wherein the phenyl ring is optionally substituted with one to two halogen, $C_{1-6}$ alkoxy or mono- or di-($C_{1-3}$ alkyl)amino, $C_{1-6}$ alkyl-$S(O)_m$, or phenyl-$S(O)_m$ wherein the phenyl ring is optionally substituted with one to two halogen, $C_{1-6}$ alkoxy, halogen or mono- or di-($C_{1-3}$ alkyl)amino;

or Z is optionally substituted with one to three amino or amino-$C_{1-3}$ alkyl wherein the N atom is optionally independently mono- or di-substituted by amino$C_{1-6}$ alkyl, $C_{1-3}$alkyl, aryl$C_{0-3}$alkyl, $C_{1-5}$ alkoxy$C_{1-3}$ alkyl, $C_{1-5}$ alkoxy, aroyl, $C_{1-3}$acyl, $C_{1-3}$alkyl-$S(O)_m$— or aryl$C_{0-3}$alkyl-$S(O)_m$— each of the aforementioned alkyl and aryl attached to the amino group is optionally substituted with one to two halogen, $C_{1-6}$ alkyl or $C_{1-6}$ alkoxy;

or Z is optionally substituted with one to three aryl, heterocycle or heteroaryl as hereinabove described in this paragraph each in turn is optionally substituted by halogen, $C_{1-6}$ alkyl or $C_{1-6}$ alkoxy;

or Z is nitrile, amino wherein the N atom is optionally independently mono- or di-substituted by $C_{1-6}$alkyl or $C_{1-3}$alkoxy$C_{1-3}$alkyl, $C_{1-6}$alkyl branched or unbranched, $C_{1-6}$alkoxy, nitrile$C_{1-4}$alkyl, $C_{1-6}$ alkyl—$S(O)_m$, aryl chosen from phenyl, pyridinyl, pyrimidinyl, pyridazinyl, pyrazinyl, imidazolyl, pyrazolyl, triazolyl, tetrazolyl, furanyl, thienyl and pyranyl each aryl being optionally substituted with one to three halogen, $C_{1-6}$ alkyl, $C_{1-6}$ alkoxy, di-($C_{1-3}$ alkyl)amino, $C_{1-6}$ alkyl—$S(O)_m$ or nitrile, and phenyl—$S(O)_m$, wherein the phenyl ring is optionally substituted with one to two halogen, $C_{1-6}$ alkoxy or mono- or di-($C_{1-3}$ alkyl)amino;

$R_1$ and $R_2$ are independently chosen from:

a $C_{1-6}$ branched or unbranched alkyl optionally partially or fully halogenated, acetyl, aroyl, $C_{1-4}$ branched or unbranched alkoxy, each being optionally partially or fully halogenated, halogen, methoxycarbonyl, $C_{1-3}$ alkyl—$S(O)_m$ optionally partially or fully halogenated, or phenylsulfonyl;

m=0, 1 or 2;

All terms as used herein in this specification, unless otherwise stated, shall be understood in their ordinary meaning as known in the art. For example, "$C_{1-6}$alkoxy" is a $C_{1-6}$alkyl with a terminal oxygen, such as methoxy, ethoxy, propoxy, pentoxy and hexoxy. All alkyl, alkenyl and alkynyl groups shall be understood as being branched or unbranched where structurally possible and unless otherwise specified. Other more specific definitions are as follows:

Ac—acetyl;
DBA—dibenzylideneacetone;
DPPF—1,1'-bis(diphenylphosphino)ferrocene;
DPPE—1,2-bis(diphenylphosphino)ethane;
DPPB—1,4-bis(diphenylphosphino)butane;
DPPP—1,3-bis(diphenylphosphino)propane;
BINAP—2,2'-bis(diphenylphosphino)-1,1'-binaphthyl;
DME—ethylene glycol dimethylether;
DMSO—dimethyl sulfoxide;
DMF—N,N-dimethylformamide;
EtO—ethoxide;
$^{i}$Pr—isopropyl;
$^{t}$Bu—tertbutyl;
THF—tetrahydrofuran;
RT or rt—room temperature;

The term "aroyl" as used in the present specification shall be understood to mean "benzoyl" or "naphthoyl".

The term "aryl" as used herein shall be understood to mean aromatic carbocycle, preferably phenyl and naphthyl, or heteroaryl.

The term "heterocycle", unless otherwise noted, refers to a stable nonaromatic 4–8 membered (but preferably, 5 or 6 membered) monocyclic or nonaromatic 8–11 membered bicyclic heterocycle radical which may be either saturated or unsaturated. Each heterocycle consists of carbon atoms and one or more, preferably from 1 to 4 heteroatoms selected from nitrogen, oxygen and sulfur. The heterocycle may be attached by any atom of the cycle, which results in the creation of a stable structure. Unless otherwise stated, heterocycles include but are not limited to, for example oxetanyl, pyrrolidinyl, tetrahydrofuranyl, tetrahydrothiophenyl, piperidinyl, piperazinyl, morpholinyl, tetrahydropyranyl, dioxanyl, tetramethylene sulfonyl, tetramethylene sulfoxidyl, oxazolinyl, thiazolinyl, imidazolinyl, tertrahydropyridinyl, homopiperidinyl, pyrrolinyl, tetrahydropyrimidinyl, decahydroquinolinyl, decahydroisoquinolinyl, thiomorpholinyl, thiazolidinyl, dihydrooxazinyl, dihydropyranyl, oxocanyl, heptacanyl, thioxanyl, dithianyl or 2-oxa- or 2-thia-5-aza-bicyclo[2.2.1]heptanyl.

The term "heteroaryl", unless otherwise noted, shall be understood to mean an aromatic 5–8 membered monocyclic or 8–11 membered bicyclic ring containing 1–4 heteroatoms such as N, O and S. Unless otherwise stated, such heteroaryls include: pyridinyl, pyridonyl, quinolinyl, dihydroquinolinyl, tetrahydroquinoyl, isoquinolinyl, tetrahydroisoquinoyl, pyridazinyl, pyrimidinyl, pyrazinyl, benzimidazolyl, benzthiazolyl, benzoxazolyl, benzofuranyl, benzothiophenyl, benzpyrazolyl, dihydrobenzofuranyl, dihydrobenzothiophenyl, benzooxazolonyl, benzo[1,4] oxazin-3-onyl, benzodioxolyl, benzo[1,3]dioxol-2-onyl, tetrahydrobenzopyranyl, indolyl, indolinyl, indolonyl, indolinonyl, phthalimidyl.

Terms which are analogs of the above cyclic moieties such as aryloxy or heteroaryl amine shall be understood to mean an aryl, heteroaryl, heterocycle as defined above attached to it's respective functional group.

As used herein, "nitrogen" and "sulfur" include any oxidized form of nitrogen and sulfur and the quaternized form of any basic nitrogen.

The term "halogen" as used in the present specification shall be understood to mean bromine, chlorine, fluorine or iodine except as otherwise noted. The compounds made by the novel processes of the invention are only those which are contemplated to be 'chemically stable' as will be appreciated by those skilled in the art. For example, a compound which would have a 'dangling valency', or 'carbanion' are not compounds made by processes contemplated by the invention.

In one embodiment of the invention there is provided a process of making the compounds of formula(A) as described hereinabove, said process comprising:

a) synthesis of a compound of formula (C) from a compound of formula (B) via substitution with an appropriate halide $X_c$. When $X_c$ is Br, methods known in the art may be utilized.

When $X_c$ is I, the present invention provides a novel process for the substitution of the leaving group (L) with iodide. This was achieved by using the conditions of $R_xCOCl$ or $(R_xCO)_2O$/metal iodide/solvent/heating (25° C.–150° C.), wherein $R_x$ is chosen from —$C_{1-7}$ alkyl, —$CF_{1-3}$ and —$CCl_{1-3}$; the metal chosen from Na and K, and the solvent chosen from acetonitrile, acetone, DMSO, DMF and THF. Preferred conditions are AcCl and NaI in acetonitrile at 70–90° C. The leaving group L is any suitable leaving group as will be appreciated by those skilled in the art, preferably L is chosen from Cl, Br, —$OCOR_y$ and —$OS(O)_mR_y$, wherein $R_y$ is aryl optionally substituted by $C_{1-4}$alkyl optionally halogenated, such as tolyl, or $R_y$ is $C_{1-4}$alkyl optionally halogenated such as $CF_3$ and $CCl_3$, L is more preferably chosen from Br and Cl.

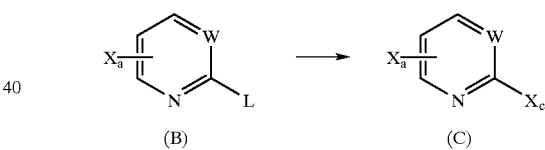

$X_a$ is chosen from Br and Cl, preferably Br;

$X_c$ is I or Br, preferably I;

$X_a$ is attached via the 4 or 5 ring position, preferably the 5 position.

b) In a one pot process, reacting a compound of the formula(C) with a Grignard reagent R—Mg—$X_b$ followed by the addition of an E-Y-Z compound wherein Y-Z is as defined above, said E-Y-Z component is further characterized as being an electrophilic derivative of Y-Z and being appropriate for Grignard reagant reactions as will be apparent to the skilled artisan, said reaction taking place in a suitable aprotic solvent at −78° C. to RT, preferably 0° C. to RT for a reaction time of ½ hour to 2 hours, preferably 1 hour, and isolating the compound of the formula (D);

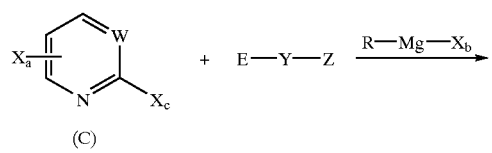

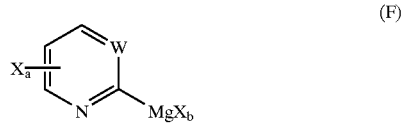

(D)

wherein:

$X_b$ is chosen from Br, Cl and I;

R is aryl, $C_{1-6}$alkyl or $C_{5-7}$cycloalkyl;

As seen in Scheme V below, this one pot novel process step provides for the formation of the Grignard reagant Compound (F):

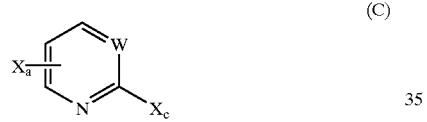

(F)

where a desirable selective formation was observed. For example the synthesis of 2-(5-halopyridyl)magnesium halides (e.g. 3 and 12) was achieved for the first time.

The process of making compounds of the formula(F) comprises:

reacting a compound of the formula(C)

(C)

with a magnesium reagent of the formula R—MgX$_b$; said reaction taking place in a suitable aprotic solvent at −78° C. to RT, for a reaction time of ½ hour to 2 hours, producing the Grignard compound of the formula(F); and wherein $X_a$, is halogen selected from Br and Cl, and $X_a$ is attached via the 4 or 5 ring position;

$X_b$ is halogen chosen from Br, Cl and I;

$X_c$ is I or Br;

W is $CR_3$ or N, wherein $R_3$ is chosen from hydrogen, $C_{1-5}$alkyl, $C_{1-5}$alkoxy, aryl$C_{0-5}$alkyl and —$COR_4$ wherein $R_4$ is chosen from $C_{1-5}$alkyl, $C_{1-5}$alkoxy, aryl$C_{0-5}$alkyl and amino which is optionally independently or di-substituted by $C_{1-5}$alkyl, and aryl$C_{0-5}$alkyl;

W is preferably CH or N;

and

R is aryl, $C_{1-6}$alkyl or $C_{5-7}$cycloalkyl.

In a preferred embodiment there is provided a process for making a compound of the formula(F) as described above and wherein W is CH;

$X_a$ is Br and attached at the 5 ring position;

$X_c$ is I;

the temperature is 0° C. to RT; and the reaction time is 1 hour.

Non-limiting examples of this reaction proceeded with complete selectivity at the 2 position in excellent yield:

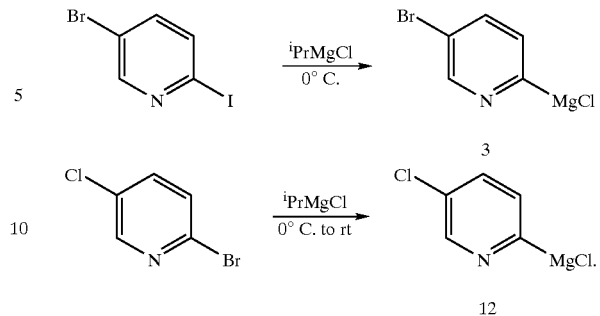

In subsequent steps, the novel process of the invention further comprises:

c) reacting the compound of the formula(D) from step b) with an aryl boronic acid of the formula (E), in the presence of a catalyst chosen from nickel and palladium. Regarding the palladium(Pd) catalyst, non-limiting examples are Pd catalysts chosen from Pd(PPh$_3$)$_2$Cl$_2$, Pd(PPh$_3$)$_4$, PdCl$_2$(DPPE), PdCl$_2$(DPPB), PdCl$_2$(DPPP), PdCl$_2$(DPPF) and Pd/C; or the combination of a palladium source and an appropriate ligand, with the Pd source, for example, being chosen from PdCl$_2$, Pd(OAc)$_2$, Pd$_2$(DBA)$_3$, Pd(DBA)$_2$, and with the ligand being chosen from PPh$_3$, DPPF, DPPP, DPPE, DPPB, P(o-tolyl)$_3$, P(2,4,6-trimethoxyphenyl)$_3$, AsPh$_3$, P($^t$Bu)$_3$, BINAP, and those bound to solid supports that are mimics of the aforementioned ligands, preferably PdCl$_2$ and PPh$_3$. Regarding the nickel(Ni) catalyst, examples of nickel (Ni) catalyst are those chosen from Ni(PPh$_3$)$_2$Cl$_2$, Ni(PPh$_3$)$_4$, NiCl$_2$(DPPE), NiCl$_2$(DPPB), NiCl$_2$(DPPP), NiCl$_2$(DPPF) and Ni/C; or the combination of a Ni source and an appropriate ligand, with the Ni source being NiCl$_2$, and with the ligand being chosen from PPh$_3$, DPPF, DPPP, DPPE, DPPB, P(o-tolyl)$_3$, P(2,4,6-trimethoxyphenyl)$_3$, AsPh$_3$, P($^t$Bu)$_3$, BINAP, and those bound to solid supports that are mimics of the aforementioned ligands. This reaction takes place in a suitable solvent such as ethylene glycol dimethyl ether (DME), THF, toluene, methylene chloride or water, preferably DME, at 0° C. to 150° C., preferably 25° C. to 100° C., for a period of 1 to 24 hours preferably about 15 hours,

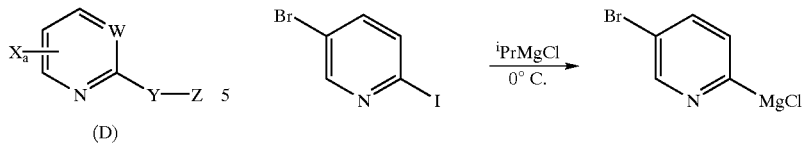

wherein P in the formula(E) is an amino protecting group such as Boc, and subsequently removing said protecting group under suitable conditions to produce a compound of the formula(A).

In a preferred embodiment of the invention there is provided a novel process of making compounds of the formula(A) as described above and wherein:

W is CH;

Ar is chosen from naphthyl, quinolinyl, isoquinolinyl, tetrahydronaphthyl, tetrahydroquinolinyl, tetrahydroisoquinolinyl, indanyl, indenyl and indolyl each being optionally substituted by one or more $R_1$ or $R_2$ groups;

Y is chosen from:

a bond and a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms; wherein when Y is the carbon chain, the left side terminal atom of Y is a carbon (the atom which is covalently attached to the heterocycle possessing W):

Z is chosen from:

phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, amino or mono- or di-($C_{1-3}$ alkyl)amino;

tetrahydropyranyl, tetrahydrofuranyl, 1,3-dioxolanonyl, 1,3-dioxanonyl, 1,4-dioxanyl, morpholinyl, thiomorpholinyl, thiomorpholinyl sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl or tetramethylene sulfonyl which are optionally substituted with one to three nitrile, $C_{1-3}$ alkyl, $C_{1-3}$ alkoxy, amino or mono- or di-($C_{1-3}$ alkyl)amino;

nitrile, $C_{1-6}$ alkyl-$S(O)_m$, halogen, $C_{1-4}$ alkoxy, amino, mono- or di-($C_{1-6}$ alkyl)amino and di-($C_{1-3}$ alkyl)aminocarbonyl;

In a more preferred embodiment of the invention there is provided a novel process of making compounds of the formula(A) as described immediately above and wherein: Ar is naphthyl;

Y is chosen from:

a bond and a $C_{1-4}$ saturated carbon chain wherein the left side terminal atom of Y is a carbon (the atom which is covalently attached to the heterocycle possessing W) and one of the other carbon atoms is optionally replaced by O, N or S and wherein Y is optionally independently substituted with an oxo group;

Z is chosen from:

phenyl, pyridinyl, pyrimidinyl, pyridazinyl, pyrazinyl, imidazolyl, dihydrothiazolyl, dihydrothiazolyl sulfoxide, pyranyl and pyrrolidinyl which are optionally substituted with one to two $C_{1-2}$ alkyl or $C_{1-2}$ alkoxy;

tetrahydropyranyl, morpholinyl, thiomorpholinyl, thiomorpholinyl sulfoxidyl, piperidinyl, piperidinonyl, piperazinyl and tetrahydropyrimidonyl which are optionally substituted with one to two $C_{1-2}$ alkyl or $C_{1-2}$ alkoxy; and $C_{1-3}$ alkoxy;

In yet a more preferred embodiment of the invention there is provided a novel process of making compounds of the formula(A) as described immediately above and wherein:

Ar is 1-naphthyl wherein the $NH_2$ is at the 4 position;

Y is chosen from:

a bond, —$CH_2$—, —$CH_2CH_2$— and —$C(O)$—,;

In an ultimately preferred embodiment of the invention there is provided a novel process of making compounds of the formula(A) as described immediately above and wherein:

Y is

—$CH_2$—;

Z is morpholinyl;

Formation of the reaction intermediate (E) can be accomplished by first protecting an aryl-amine followed by boronic acid formation through a sequence of metal-bromine exchange, quenching with trialkylborate and hydrolysis, as can be seen in Scheme V in the conversion of 7 to 9. Compounds of the formula (E) possessing other desired Ar can be accomplished without undue experimentation by variations apparent to those of ordinary skill in the art in view of the teachings in this specification and the state of the art.

A desirable novel feature of the process of the invention is the selective formation of a 2-(5-halopyridyl) or 2-(5-halopyrimidinyl) magnesium halides, preferably 2-(5-halopyridyl) magnesium halides (e.g. 3 and 12, vide infra), and their subsequent reactions with the in situ generated E-Y-Z electrophiles. Below in Scheme 1, the addition of 2-(5-halopyridyl) magnesium halide 3 to the immonium salt 6 was carried out without the isolation of the immonium salt.

A non-limiting example for a compound of the formula (A) is the amine 1 shown in Scheme V.

Scheme V

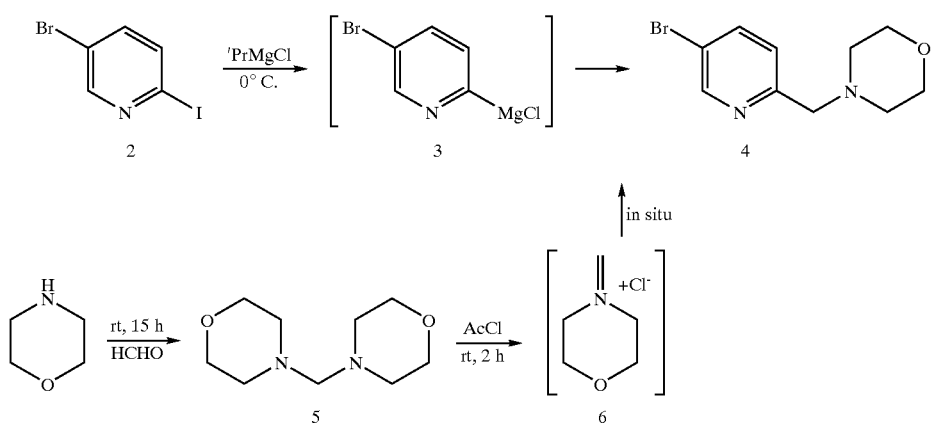

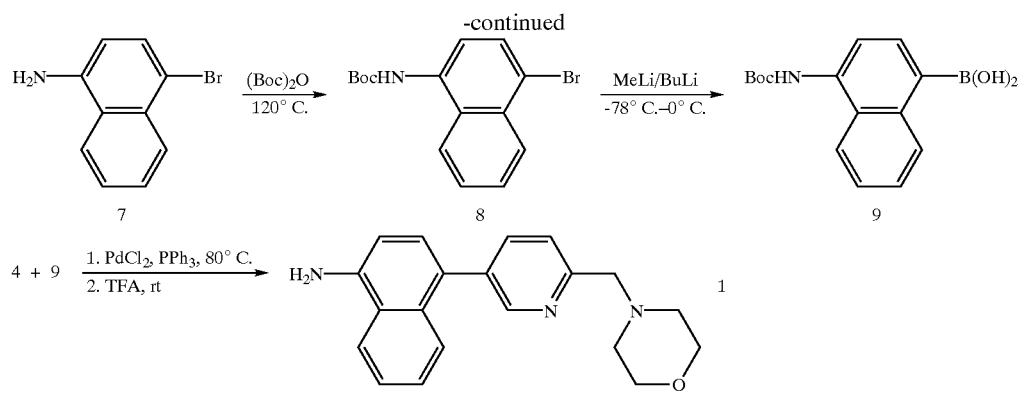

Reaction intermediate (2) with a generic formula (B) above can be obtained as exemplified in Scheme VI below. Addition of a copper catalyst may be required for transformations involving certain types of electrophiles, for example the alkylation reaction of the Grignard intermediate with various alkyl halides and epoxides.

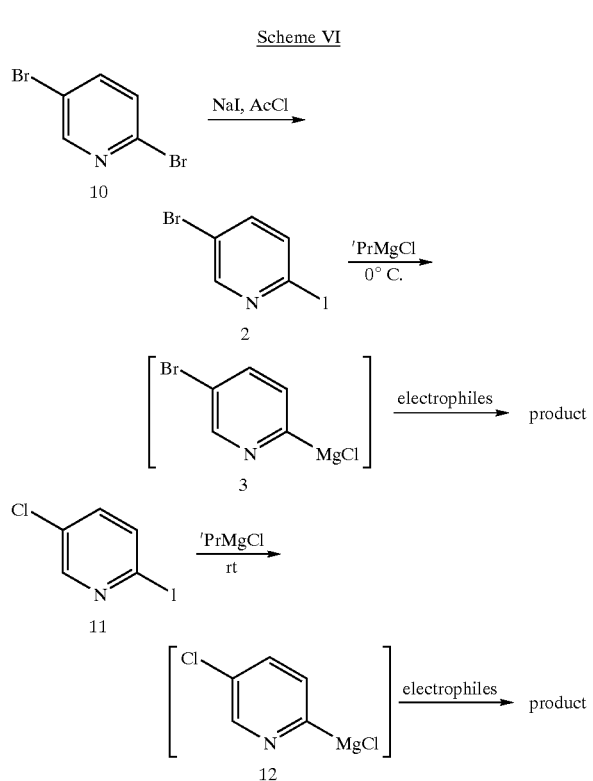

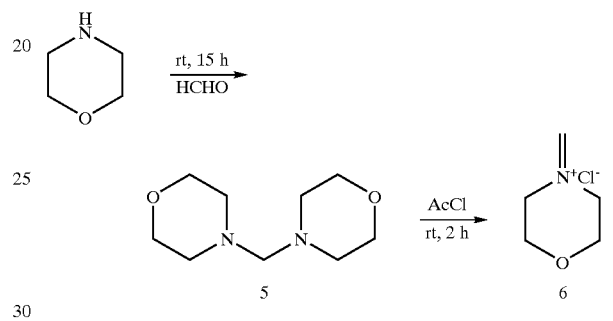

Examples of appropriate electrophiles are shown in the table below. Methods of making Y-Z electrophilic derivatives are within the skill in the art. Y component in Y-Z is a derivative of the Y of the formula (A) of the final product upon the addition of the electrophile to the Grignard intermediate. Products may be further derivatized to achieve the desired Y-Z. Such further transformations are within the skills in the art. A non-limiting example is shown below for a preferred embodiment of Z in the formula (A), i.e., the morpholino immonium salt 6. Reference in this regard may be made to Heaney, H.; Papageorgiou, G.; Wilkins, R. F. *Tetrahedron* 1997, 53, 2941; Sliwa, H.; Blondeau, D. *Heterocycles* 1981, 16, 2159;.

In this example, E-Y-Z is compound 6, wherein morpholinyl represents Z and Y is —CH$_2$— in the final product.

As described above, any electrophile represented by Y, possessing a Z component and compatible with Grignard type reactions are contemplated to be within the scope of the invention. Additional non-limiting examples of E-Y-Z are:

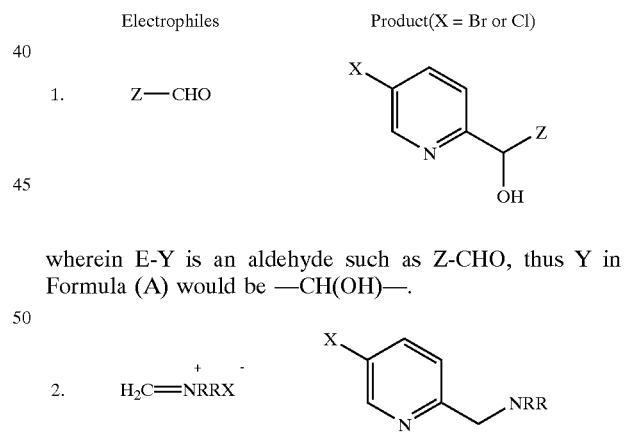

wherein E-Y is an aldehyde such as Z-CHO, thus Y in Formula (A) would be —CH(OH)—.

wherein NRR represent any of the above-listed Z amine moieties or heterocycles possessing a nitrogen heteroatom and Y can be alkylene such as —CH$_2$—, X is a countervalent anion.

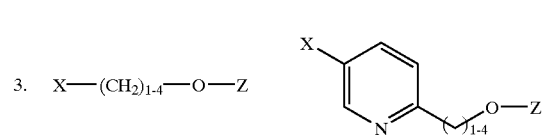

wherein E-Y is a branched or unbranched alkoxy possessing a halogen atom X and further linked to Z, such as ClCH$_2$—O-Z.

4. 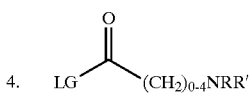  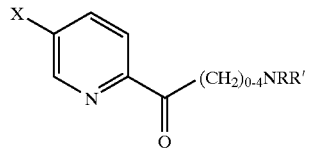

wherein E-Y is a C$_{1-4}$acyl halide such as formylchloride, NRR' represents any of the above-listed Z amine moieties, or heterocycles possessing a nitrogen heteroatom. LG is an appropriate leaving group such as halogens. (see: Katritzky et al., *J. Chem. Res.* 1999, 3, 230.)

5. 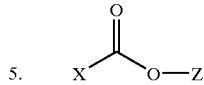  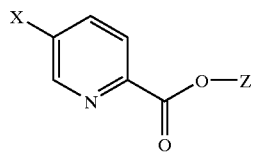

wherein E-Y is a haloester moiety such as chloroformate. X is an appropriate leaving group such as halogens or alkoxy groups. (see: Satyanarayana et al., *Synth. Commun.* 1990, 20 (21), 3273.)

6. Z—Y—X wherein an appropriate Z-Y is substituted by halogen X, preferably iodine, such as CH$_3$I.

7. 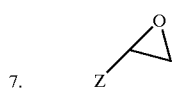  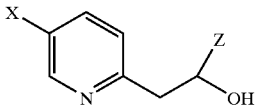

Addition of an appropriate Z attached to a reactive epoxide provides the hydroxy intermediate which is further derivatized to the desired Y component.

8. 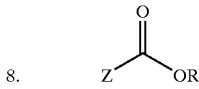  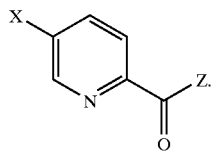

Acylation wherein Y is an acyl attached to Z may be accomplished via the appropriate acylation reagent such as the ester shown above wherein —OR is a known leaving group.

In another embodiment of the invention there is provided a process of making the compounds of formula(A):

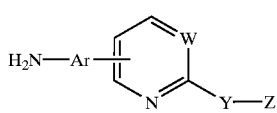

(A)

wherein Ar and W are as described above;
and wherein for the formula(A):
Y is —CH$_2$—; and Z is chosen from:
heterocycle chosen from morpholinyl, thiomorpholinyl, piperidinyl and pyrrolidinyl each of the aforementioned Z are optionally substituted with one to three halogen, C$_{1-6}$ alkyl, C$_{1-6}$ alkoxy, C$_{1-3}$ alkoxy-C$_{1-3}$ alkyl, C$_{1-6}$ alkoxycarbonyl, aroyl, C$_{1-3}$acyl, oxo, pyridinyl-C$_{1-3}$ alkyl, imidazolyl-C$_{1-3}$ alkyl, tetrahydrofuranyl-C$_{1-3}$ alkyl, nitrile-C$_{1-3}$ alkyl, nitrile, phenyl wherein the phenyl ring is optionally substituted with one to two halogen, C$_{1-6}$ alkoxy, di-(C$_{1-3}$ alkyl)amino, C$_{1-6}$ alkyl-S(O)$_m$, or phenyl-S(O)$_m$ wherein the phenyl ring is optionally substituted with one to two halogen, C$_{1-6}$ alkoxy or di-(C$_{1-3}$ alkyl)amino;

or Z is optionally substituted with one to three one to three amino or amino-C$_{1-3}$ alkyl wherein the N atom is optionally independently di-substituted by aminoC$_{1-6}$ alkyl, C$_{1-3}$alkyl, arylC$_{0-3}$alkyl, C$_{1-5}$ alkoxyC$_{1-3}$ alkyl, C$_{1-5}$ alkoxy, aroyl, C$_{1-3}$acyl, C$_{1-3}$alkyl-S(O)$_m$— or arylC$_{0-3}$alkyl-S(O)$_m$— each of the aforementioned alkyl and aryl attached to the amino group is optionally substituted with one to two halogen, C$_{1-6}$ alkyl or C$_{1-6}$ alkoxy;

or Z is optionally substituted with one to three aryl or heterocycle as hereinabove described in this paragraph each in turn is optionally substituted by halogen, C$_{1-6}$ alkyl or C$_{1-6}$ alkoxy;

or Z is amino wherein the N atom is optionally independently mono- or di-substituted by C$_{1-6}$alkyl or C$_{1-3}$alkoxyC$_{1-3}$alkyl, C$_{1-6}$alkyl branched or unbranched, C$_{1-6}$alkoxy, nitrileC$_{1-4}$alkyl, C$_{1-6}$ alkyl-S(O)$_m$, aryl chosen from phenyl, pyridinyl, pyrimidinyl, pyridazinyl, pyrazinyl, imidazolyl, pyrazolyl, triazolyl, tetrazolyl, furanyl, thienyl and pyranyl each aryl being optionally substituted with one to three halogen, C$_{1-6}$ alkyl, C$_{1-6}$ alkoxy, di-(C$_{1-3}$ alkyl)amino, C$_{1-6}$ alkyl-S(O)$_m$ or nitrile, and phenyl-S(O)$_m$, wherein the phenyl ring is optionally substituted with one to two halogen, C$_{1-6}$ alkoxy or mono- or di-(C$_{1-3}$ alkyl)amino;

said reaction comprising:
reacting a compound of the formula(C)

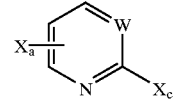

(C)

with a magnesium reagent of the formula R—MgX$_b$; said reaction taking place in a suitable aprotic solvent at −78° C. to RT, for a reaction time of ½ hour to 2 hours producing the Grignard compound(F):

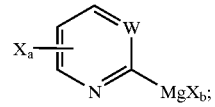

(F)

wherein
X$_a$, is halogen selected from Br and Cl, and X$_a$ is attached to the ring via the 4 or 5 position;
X$_b$ is halogen chosen from Br, Cl and I;
X$_c$ is I or Br;
W is CH, CCH$_3$ or N; and
R is aryl, C$_{1-6}$alkyl or C$_{5-7}$cycloalkyl;

subsequently reacting the Grignard compound from the prior step with a N,N-dialkylformamide such as DMF to form an aldehyde:

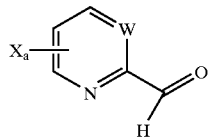

and isolating the aldehyde;

reacting the aldehyde with an appropriate Z group under nucleophilic addition conditions to provide the compound

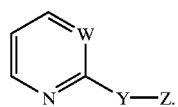
(D)

This transformation is within the skill in the art and involves reacting of the aldehyde and the appropriate Z component under acidic conditions such as HCl, AcOH, $H_2SO_4$ etc, preferably AcOH, in a suitable solvent such as THF, methylene chloride, 1,2-dichloroethane, preferably 1,2-dichloroethane for 0.5–5 h (preferably 2 h) at about RT followed by in situ reduction for 0.5–5 h (preferably 2 h) to provide the product (D).

Subsequent addition of the $NH_2$—Ar compound can be done as described hereinabove, to provide the final product compound of the formula(A) as described above in this embodiment of the invention. A non-limiting example of this embodiment of the invention is shown in Scheme VII.

Scheme VII

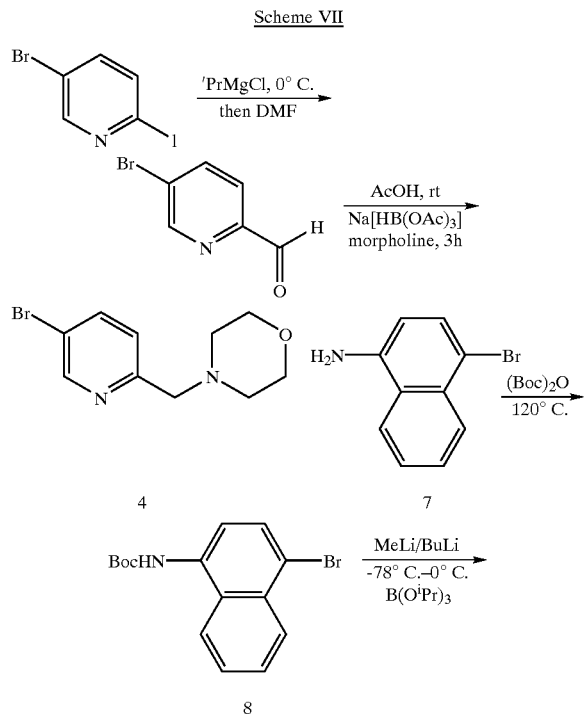

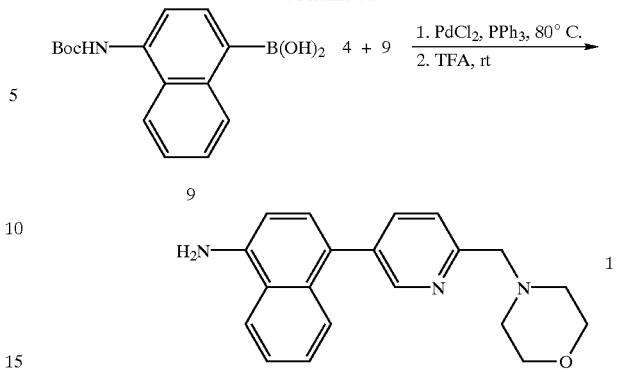

In order that this invention be more fully understood, the following examples are set forth. These examples are for the purpose of illustrating preferred embodiments of this invention, and are not to be construed as limiting the scope of the invention in any way.

SYNTHETIC EXAMPLES

Example 1

Synthesis of 5-bromo-2-iodopyridine from 2,5-dibromopyridine 2,5-Dibromopyridine (100 g) was suspended in acetonitrile (500 mL) at rt. NaI (94 g) and AcCl (45 mL) were added and the reaction was then gently refluxed for 3 h. An aliquot was analyzed by $^1$H NMR and MS and the reaction was about 80% complete. The reaction was cooled to rt and quenched with a few mL of water and then $K_2CO_3$ aqueous solution to pH 8. EtOAc (1.5 L) was added to extract the organic materials. The organic layer was washed with saturated $NaHSO_3$ solution, the brine, and then dried over $MgSO_4$. Concentration gave crude material that was subjected to the same conditions for about 3 h at which time $^1$H NMR showed that the reaction was greater than 97% complete. The same workup provided the crude material. The crude crystals were washed twice with $CH_3CN$ and dried in the oven. The yield was 95 g.

$^1$H NMR (CDCl$_3$, 400 MHz) δ8.44 (s, 1H), 7.60 (d, J=8.26 Hz, 1H), 7.44 (d, J=8.25 Hz, 1H).

Example 2

Synthesis of 5-bromo-2-formylpyridine from 5-bromo-2-iodopyridine via the Grignard Intermediate In a 22 L 3-neck round bottomed flask equipped with a mechanical stirrer, 1 kg (3.52 mol) of 2-iodo-5-bromopyridine was dissolved in 5 L of THF. The solution was cooled to about −15 to −10° C. 1.9 L (2 M, 380 mol, 1.08 eq) of $^i$PrMgCl was added at a rate to keep the internal temperature below 0° C. The reaction mixture became a brown suspension. After the reaction mixture was stirred between −15 to 0° C. for 1 h, 400 mL (5.16 mol, 1.5 eq) of DMF was added at a rate to keep the internal temperature below 0° C. After stirring at this temperature for 30 min, the cooling bath was removed and the reaction was allowed to warm to room temperature over 1 h. The reaction mixture was then cooled to 0° C. and 4.0 L (7.74 mol, 2.2 eq) of 2 N HCl was added at a rate to keep the internal temperature below 25° C. The mixture was stirred for 30 min, then pH was raised from 1 to a pH 6–7 by adding about 150 mL of 2 N NaOH. The layers were separated and the THF layer was concentrated to give dark brown wet solids. The aqueous layer was extracted with 3 L of CH$_2$Cl$_2$. The CH$_2$Cl$_2$ layer was used to dissolve the residue obtained from the THF layer, the resulting solution was washed with water (2×2 L), dried by stirring with MgSO$_4$ (400 g) for 30 min, and filtered. Concentration of the filtrate to dryness gave 583 g of the desired aldehyde as brownish-yellow solids (89% yield after air drying).

$^1$H NMR (CDCl$_3$, 400 MHz) δ10.04 (d, J=0.68 Hz, 1H), 8.86 (t, J=0.52 Hz, 1H), 8.02 (dt, J=8.20, 0.68 Hz, 1H), 7.85 (d, J=8.48 Hz, 1H).

Example 3
Synthesis of 5-bromo-2-(4-morpholinylmethyl)pyridine from 5-bromo-2-iodopyridine via the Grignard Intermediate To a solution of bis(1-morpholinyl)methane (130 mg) in THF (3 mL) at rt was added acetyl chloride (45 mL). The reaction was stirred for 1 h and cooled to 0° C.

In another flask, 5-bromo-2-iodopyridine (130 mg) was dissolved in THF (3 mL) at −40° C. The solution was treated with $^i$PrMgCl (2 M in THF, 0.39 mL) at the same temperature for 15 min. Then the Grignard solution was cannulated into the immonium salt suspension generated above at 0° C. After the addition, the reaction mixture was stirred at rt for 1 h and quenched with saturated NH$_4$Cl solution. Extraction with CH$_2$Cl$_2$, drying over MgSO$_4$, filtration and concentration gave a crude oil. This was further purified by column chromatography to afford the product in about 50% yield.

$^1$H NMR (CDCl$_3$, 400 MHz) δ8.60 (s, 1H), 7.76 (d, J=8.24 Hz, 1H), 7.32 (d, J=8.64 Hz, 1H), 3.72 (m, 4H), 3.59 (s, 2H), 2.48 (m, 4H).

Example 4
Synthesis of 5-bromo-2-(4-morpholinyl)methylpyridine from 5-bromo-2-formylpyridine To a solution of 500 g (2.688 moles) aldehyde in a 5 L of 1,2-dichloroethane at room temperature was added morpholine (1.15 eq, 3.09 moles, 269 ml) in one portion. The reaction temperature went up to 29° C. After stirring the reaction mixture for 15 min, acetic acid (2.1 eq, 5.6 moles, 323 mL) was added in one portion. The temperature rose to 31° C. It was stirred for 1.5 h at room temperature. Sodium triacetoxyborohydride (1.06 eq, 2.85 moles, 604 g ) was added in 100 g portions every 10 min. The temperature was maintained between 35° C. and 46° C. by gentle cooling. It was stirred for an additional 2 h.

The reaction mixture was quenched with 4 N HCl keeping the temperature below 15° C. At the end of addition, the pH of aqueous phase was between 0 and 1 (~2200 mL). The organic phase was separated and discarded. The aqueous phase was basified with 9 N NaOH (~740 g NaOH) to pH ~9.5 keeping the internal temperature below 15° C. The product was extracted with methylene chloride. Evaporation of the solvent gave pure amine (660 g, 2.57 moles).

Example 5
Synthesis of 5-Bromo-3-methyl-2-pyridinecarboxaldehyde

An example of the synthesis of a compound of formula (F) in which W is CR$_3$ (R$_3$=methyl), and subsequent reaction with an electrophile is provided below and illustrated in Scheme VIII.

Scheme VIII

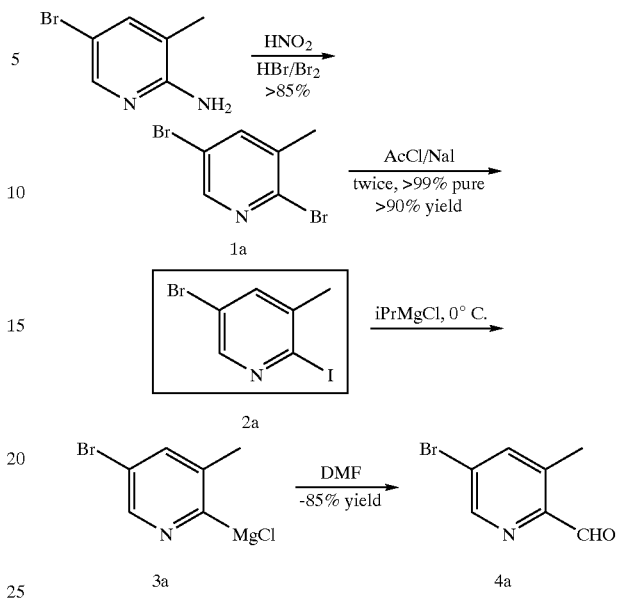

2,5-Dibromo-3-picoline is commercially available or may be prepared from 2-amino-5-bromo-3-methylpyridine by standard diazotization followed by bromination in Br$_2$/HBr. Acetyl chloride (0.68 mol, 52.7 mL) was added to a stirring solution of 2,5-dibromo-3-picoline (0.45 mol, 113 g) in acetonitrile (600 mL) followed by sodium iodide (1.66 mol, 250 g) and the reaction mixture was gently refluxed for 18 h. The cooled reaction mixture was filtered and the solid was washed with acetonitrile until colorless. It was suspended in methylene chloride and treated with aq. Na$_2$CO$_3$ until the pH was 10–11. The organic layer was separated, dried over anhydrous sodium sulfate and concentrated to give a brown oil. It was subjected to iodination a second time as above (reflux time 6 h). A dark brown oil was obtained using the same work-up as above. A solution of this oil in hexane was treated with charcoal, filtered and concentrated to give a light brown oil. It slowly solidified on standing to give 5-bromo-2-iodo-3-methylpyridine as a light brown solid (95.0 g, 0.32 mol). Yield: 70%.

2-Iodo-5-bromo-3-methylpyridine (250 mg) was dissolved in THF (4.0 mL). The solution was cooled to 0° C. $^i$PrMgCl (2 M in THF, 0.5 mL) was added at a rate to keep the internal temperature below 5° C. After the reaction mixture was stirred at 0° C. for 1 h, DMF (0.13 mL) was added at 0° C. After stirring at this temperature for 30 min, the cooling bath was removed and the reaction was allowed to warm to room temperature over 1 h. The reaction mixture was hydrolyzed by a saturated aqueous NH$_4$Cl solution. Then the aqueous layer was extracted with CH$_2$Cl$_2$. The CH$_2$Cl$_2$ layer was dried over MgSO$_4$ and concentrated to give the desired aldehyde as a brownish-yellow solid (80% yield).

Example 6

Improved Synthesis of Pyridyl Intermediate: 5-bromo-2-(4-morpholinylmethyl)pyridine Using Solvent: Methylene Chloride

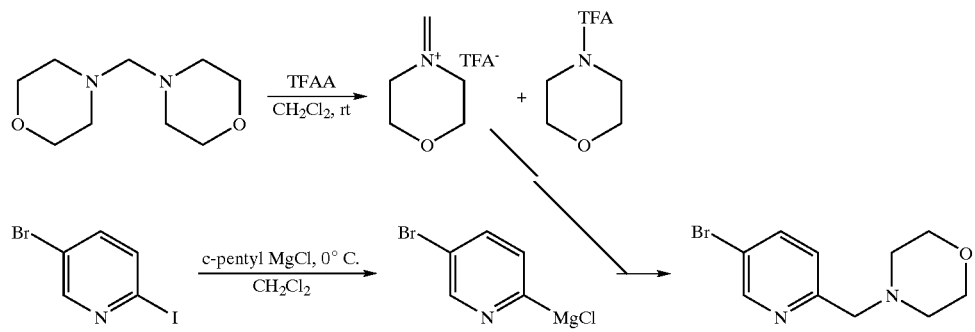

To a stirred solution of 20 g (70.4 mmole) of 5-bromo-2-iodopyridine in 140 mL of methylene chloride at 0° C. was added 37 mL of cyclopentyl magnesium chloride (2 M in ether). The exchange reaction was complete within 45 min. In a separate vessel, 14.4 g (77 mmole) of dimorpholinomethane was dissolved in 180 mL of methylene chloride at rt. Then 10.4 mL (74 mmole) of TFAA was added and stirred for 0.5 h to furnish the salt solution. The Grignard solution was cannulated into the TFA salt solution while maintaining the internal T<25° C. The reaction was stirred at rt for 0.5 h. The reaction was quenched with 150 mL of NH$_4$Cl (saturated aq) and layers were separated. The organic layer was washed with 30 mL×3 of 1.5 N HCl (aq). To the combined aqueous layer was added 5 mL of heptane and it was then neutralized using 10 N NaOH to pH 12 at 0° C. with vigorous agitation. A few seed crystals were added to induce crystallization. After 2 h stirring at 0° C., the mixture was filtered to give the product as a light yellow crystalline compound (11.2 g, 62% yield).

What is claimed is:

1. A process of making a compound of the formula:

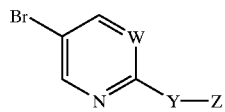

wherein:
W is CR$_3$ or N, wherein R$_3$ is chosen from hydrogen, C$_{1-5}$alkyl, C$_{1-5}$alkoxy, arylC$_{0-5}$alkyl;

Y is chosen from
a bond, C$_{1-4}$ saturated or unsaturated branched or unbranched carbon chain optionally partially or fully halogenated, wherein one or more methylene groups are optionally replaced by O, N, or S(O)$_m$ and wherein Y is optionally independently substituted with one to two oxo groups, phenyl or one or more C$_{1-4}$ alkyl optionally substituted by one or more halogen atoms; wherein when Y is the carbon chain, the left side terminal atom of Y is a carbon;

Z is chosen from:
aryl, heteroaryl chosen from pyridinyl, piperazinyl, pyrimidinyl, pyridazinyl, pyrazinyl, imidazolyl, pyrazolyl, triazolyl, furanyl, thienyl and pyranyl, heterocycle chosen from tetrahydropyrimidonyl, cyclohexanonyl, cyclohexanolyl, 2-oxa- or 2-thia-5-aza-bicyclo[2.2.1]heptanyl, pentamethylene sulfidyl, pentamethylene sulfoxidyl, pentamethylene sulfonyl, tetramethylene sulfidyl, tetramethylene sulfoxidyl or tetramethylene sulfonyl, tetrahydropyranyl, tetrahydrofuranyl, 1,3-dioxolanonyl, 1,3-dioxanonyl, 1,4-dioxanyl, morpholinyl, thiomorpholinyl, thiomorpholinyl sulfoxidyl, thiomorpholinyl sulfonyl, piperidinyl, piperidinonyl, pyrrolidinyl and dioxolanyl, each of the aforementioned Z are optionally substituted with one to three halogen, C$_{1-6}$ alkyl, C$_{1-6}$ alkoxy, C$_{1-3}$ alkoxy-C$_{1-3}$ alkyl, C$_{1-6}$ alkoxycarbonyl, aroyl, C$_{1-3}$acyl, oxo, pyridinyl-C$_{1-3}$ alkyl, imidazolyl-C$_{1-3}$ alkyl, tetrahydrofuranyl-C$_{1-3}$ alkyl, nitrile-C$_{1-3}$ alkyl, nitrile, phenyl wherein the phenyl ring is optionally substituted with one to two halogen, C$_{1-6}$ alkoxy or mono- or di-(C$_{1-3}$ alkyl)amino, C$_{1-6}$ alkyl-S(O)$_m$, or phenyl-S(O)$_m$ wherein the phenyl ring is optionally substituted with one to two halogen, C$_{1-6}$ alkoxy, halogen or mono- or di-(C$_{1-3}$ alkyl)amino;

or Z is optionally substituted with one to three amino or amino-C$_{1-3}$ alkyl wherein the N atom is optionally independently mono- or di-substituted by aminoC$_{1-6}$ alkyl, C$_{1-3}$alkyl, arylC$_{0-3}$alkyl, C$_{1-5}$ alkoxyC$_{1-3}$ alkyl, C$_{1-5}$ alkoxy, aroyl, C$_{1-3}$acyl, C$_{1-3}$alkyl-S(O)$_m$— or arylC$_{0-3}$alkyl-S(O)$_m$— each of the aforementioned alkyl and aryl attached to the amino group is optionally substituted with one to two halogen, C$_{1-6}$ alkyl or C$_{1-6}$ alkoxy; or Z is optionally substituted with one to three aryl, heterocycle or heteroaryl as hereinabove described in this paragraph each in turn is optionally substituted by halogen, C$_{1-6}$ alkyl or C$_{1-6}$ alkoxy;

or Z is nitrite, amino wherein the N atom is optionally independently mono- or di-substituted by C$_{1-6}$alkyl or C$_{1-3}$alkoxyC$_{1-3}$alkyl, C$_{1-6}$alkyl branched or unbranched, C$_{1-6}$alkoxy, nitrileC$_{1-4}$alkyl, C$_{1-6}$ alkyl-S(O)$_m$, aryl chosen from phenyl, pyridinyl, pyrimidinyl, pyridazinyl, pyrazinyl, imidazolyl, pyrazolyl, triazolyl, tetrazolyl, furanyl, thienyl and pyranyl each aryl being optionally substituted with one to three halogen, C$_{1-6}$ alkyl, C$_{1-6}$ alkoxy, di-(C$_{1-3}$ alkyl)amino, C$_{1-6}$ alkyl-S(O)$_m$ or nitrite, and phenyl-S(O)$_m$, wherein the phenyl ring is optionally substituted with one to two halogen, C$_{1-6}$ alkoxy or mono- or di-(C$_{1-3}$ alkyl)amino;

m=0, 1 or 2;

said process comprising:
i) in a one pot process, reacting a compound of the formula(C) with a Grignard reagent R—Mg—X$_b$ followed by the addition of an E-Y-Z compound wherein Y-Z is as defined above, said E-Y-Z component is further characterized as being an electrophilic derivative of Y-Z, said reaction taking place in a methylene chloride at −78° C. to RT, for a reaction time of ½ hour to 2 hours, and isolating the product compound;

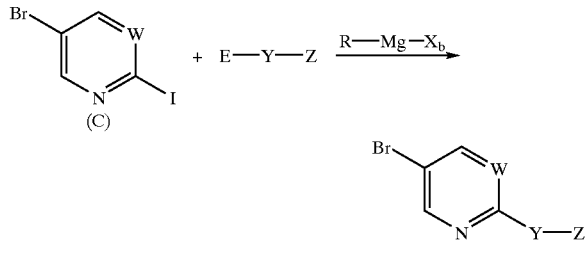

wherein:

$X_b$ is chosen from Br, Cl and I;

R is chosen from aryl, $C_{1-6}$alkyl and $C_{5-7}$cycloalkyl.

2. The process according to claim 1 wherein W is CH or N.

3. The process according to claim 2 wherein:

in step i):

the reaction temperature is preferably 0° C. to RT;

the reaction time is 1 hour;

R is $C_{1-6}$alkyl.

4. The process according to claim 3, in step i) R is c-pentyl.

5. The process according to claim 4 wherein:

W is CH;

Y is chosen from:

a bond and a $C_{1-4}$ saturated or unsaturated carbon chain wherein one of the carbon atoms is optionally replaced by O, N, or $S(O)_m$ and wherein Y is optionally independently substituted with one to two oxo groups, phenyl or one or more $C_{1-4}$ alkyl optionally substituted by one or more halogen atoms; wherein when Y is the carbon chain, the left side terminal atom of Y is a carbon (the atom which is covalently attached to the heterocycle possessing W)

Z is chosen from:

phenyl, pyridinyl, pyrimidinyl, pyridazinyl, pyrazinyl, imidazolyl, furanyl, thienyl, dihydrothiazolyl, dihydrothiazolyl sulfoxidyl, pyranyl, pyrrolidinyl which are optionally substituted with one to three nitrile, $C_{1-3}$ alkyl, $C_{1-3}$ alkoxy, amino or mono- or di-($C_{1-3}$ alkyl) amino;

tetrahydropyranyl, tetrahydrofuranyl, 1,3-dioxolanonyl, 1,3-dioxanonyl, 1,4-dioxanyl, morpholinyl, thiomorpholinyl, thiomorpholinyl sulfoxidyl, piperidinyl, piperidinonyl, piperazinyl, tetrahydropyrimidonyl, pentamethylene sulfidyl, pentamethylene sulfoxidyl, pentamethylene sulfonyl, tetramethylene sulfidyl, tetramethylene sulfoxidyl and tetramethylene sulfonyl which are optionally substituted with one to three nitrile, $C_{1-3}$ alkyl, $C_{1-3}$ alkoxy, amino or mono- or di-($C_{1-3}$ alkyl)amino;

nitrile, $C_{1-6}$ alkyl-$S(O)_m$, halogen, $C_{1-4}$ alkoxy, amino, mono- or di-($C_{1-6}$ alkyl)amino and di-($C_{1-3}$ alkyl) aminocarbonyl.

6. The process according to claim 5 wherein:

Y is chosen from:

a bond and a $C_{1-4}$ saturated carbon chain wherein the left side terminal atom of Y is a carbon (the atom which is covalently attached to the heterocycle possessing W) and one of the other carbon atoms is optionally replaced by O, N or S and wherein Y is optionally independently substituted with an oxo group;

Z is chosen from:

phenyl, pyridinyl, pyrimidinyl, pyridazinyl, pyrazinyl, imidazolyl, dihydrothiazolyl, dihydrothiazolyl sulfoxide, pyranyl and pyrrolidinyl which are optionally substituted with one to two $C_{1-2}$ alkyl or $C_{1-2}$ alkoxy;

tetrahydropyranyl, morpholinyl, thiomorpholinyl, thiomorpholinyl sulfoxidyl, piperidinyl, piperidinonyl, piperazinyl and tetrahydropyrimidonyl which are optionally substituted with one to two $C_{1-2}$ alkyl or $C_{1-2}$ alkoxy; and $C_{1-3}$ alkoxy.

7. The process according to claim 6 wherein:

Y is chosen from:

a bond, —$CH_2$—, —$CH_2CH_2$— and —C(O)—.

8. The process according to claim 7 wherein

The temperature is 0° C., $X_b$ is Cl and

—Y-Z is:

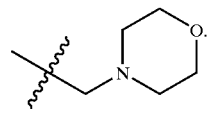

* * * * *